United States Patent [19]

Wiegers et al.

[11] 4,301,076
[45] Nov. 17, 1981

[54] ISOCHROMAN MUSK COMPOUNDS AND ORGANOLEPTIC USES THEREOF

[75] Inventors: Wilhelmus J. Wiegers, Red Bank; Mark A. Sprecker, Sea Bright; Hugh Watkins, Lincroft; Manfred H. Vock, Locust; Frederick L. Schmitt, Holmdel, all of N.J.

[73] Assignee: International Flavors & Fragrances Inc., New York, N.Y.

[21] Appl. No.: 206,577

[22] Filed: Nov. 13, 1980

Related U.S. Application Data

[62] Division of Ser. No. 63,374, Aug. 3, 1979, Pat. No. 4,250,200.

[51] Int. Cl.$^3$ .......................................... C07D 311/78
[52] U.S. Cl. .................................................. 260/345.2
[58] Field of Search ....................................... 260/345.2

[56] References Cited

U.S. PATENT DOCUMENTS

| | | | |
|---|---|---|---|
| 3,360,530 | 12/1967 | Heeringa et al. | 260/345.2 |
| 3,532,719 | 10/1970 | Theimer | 260/345.2 |
| 3,910,964 | 10/1975 | Sanders et al. | 260/345.2 |
| 3,978,090 | 8/1976 | Sanders et al. | 260/345.2 |
| 4,162,256 | 7/1979 | Sprecker et al. | 260/345.2 |

Primary Examiner—Nicky Chan
Attorney, Agent, or Firm—Arthur L. Liberman

[57] ABSTRACT

Processes and compositions are described for the use in foodstuff flavor and aroma and perfume and perfumed article aroma augmenting, modifying, altering, and enhancing compositions and as foodstuff, chewing gum, toothpaste, medicinal product, perfume and perfumed article aroma imparting materials of indane alkanols and tricyclic isochromans defined according to the generic structure:

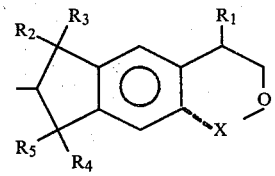

wherein $R_1$ is hydrogen or methyl; $R_2$, $R_3$, $R_4$ and $R_5$ represent hydrogen, methyl or isopropyl; the dashed line represents a carbon-carbon single bond or no bond; X represents —CH$_2$—, CH$_3$ or hydrogen; with the proviso (i) that $R_2$ and $R_3$ represent methyl when $R_4$ is hydrogen and $R_5$ is isopropyl and $R_4$ and $R_5$ represent methyl when $R_2$ is hydrogen and $R_3$ is isopropyl; and the dashed line represents a carbon-carbon single bond when X is —CH$_2$— and the dashed line represents no bond when X is hydrogen or CH$_3$.

Addition of said indane alkanols and tricyclic isochromans or mixtures thereof is indicated to produce:
  (a) In food flavorings, a sweet, musky aroma and taste; and
  (b) In perfumes and perfumed articles and colognes, a sweet, musk aroma.

1 Claim, 16 Drawing Figures

GLC PROFILE FOR EXAMPLE III.

GLC PROFILE FOR EXAMPLE I

NMR SPECTRUM FOR EXAMPLE I.

CMR SPECTRU FOR EXAMPLE I.

IR SPECTRUM FOR EXAMPLE I.

GLC PROFILE FOR EXAMPLE II.

NMR SPECTRUM FOR EXAMPLE III.

IR SPECTRUM FOR EXAMPLE III.

FIG.II
GLC PROFILE FOR EXAMPLE IV.
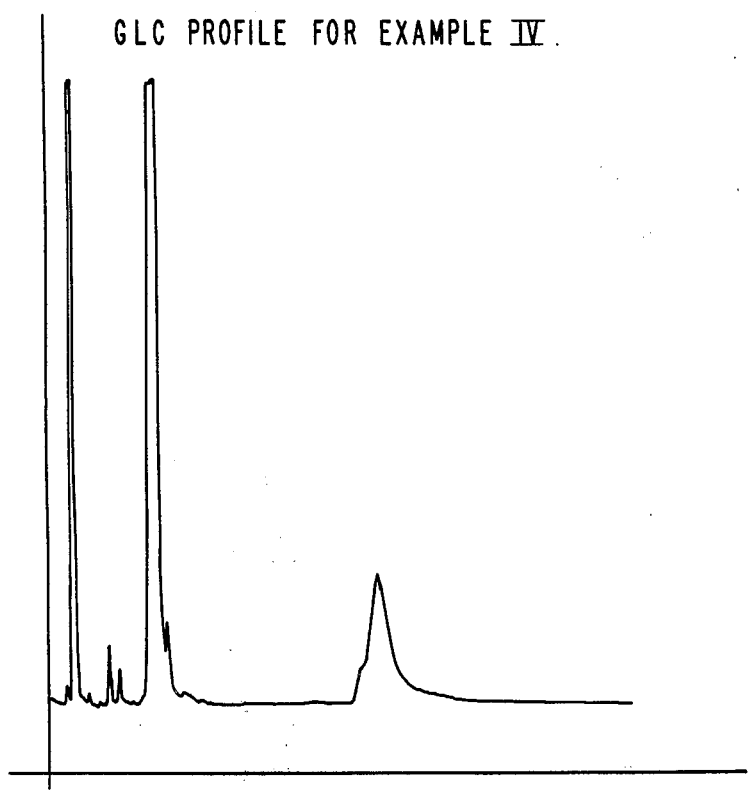
NMR SPECTRUM FOR EXAMPLE IV.
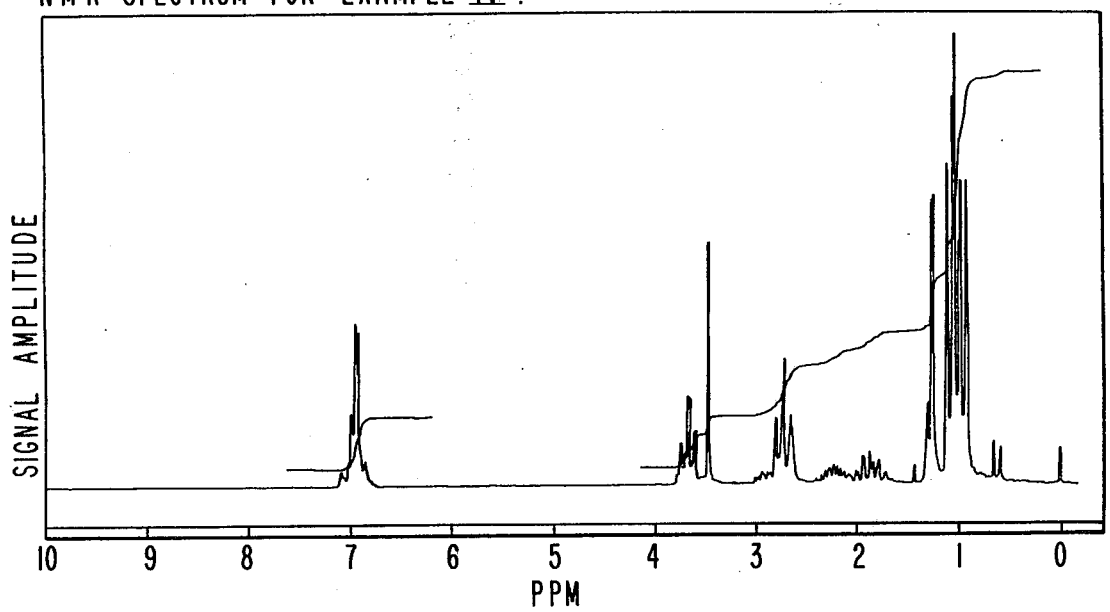
FIG.12

IR SPECTRUM FOR EXAMPLE IV.

GLC PROFILE FOR EXAMPLE V.

NMR SPECTRUM FOR EXAMPLE V.

IR SPECTRUM FOR EXAMPLE V.

ISOCHROMAN MUSK COMPOUNDS AND ORGANOLEPTIC USES THEREOF

This application is a divisional of application for United States Letters Pat. Ser. No. 63,374 filed on Aug. 3, 1979, now U.S. Pat. No. 4,250,200 issued on Feb. 10, 1981.

BACKGROUND OF THE INVENTION

The present invention relates to indane alkanols and tricyclic isochromans and mixtures containing same as well as organoleptic uses thereof to alter, modify, augment, enhance or impart flavors and/or aromas in (or to) consumable materials.

There has been considerable work performed relating to substances which can be used to impart (or alter, modify or enhance) flavors and fragrances to (or in) various consumable materials. These substances are used to diminish the use of natural materials, some of which may be in short supply and to provide more uniform properties in the finished product. Sweet and musky aroma characteristics and sweet and musky flavor characteristics are particularly desirable for many uses in foodstuff flavors, particularly pear, apricot and peach flavors. Musky aromas are desirable in several types of perfume compositions and for use in perfumed articles.

The production of isochromans has been shown in the prior art and certain novel isochromans have recently been disclosed with an outstanding musk fragrance. Such isochromans especially adapted for perfumery by virtue of their fragrance properties have been disclosed in Heeringa and Beets, U.S. Pat. No. 3,360,530 issued on Dec. 26, 1967.

A number of routes have been shown to be available for the production of isochromans, such as those set forth in U.S. Pat. No. 3,360,530 and one of the most straight forward of these routes is treatment of a Friedel Crafts reactant with an alkylene oxide under Friedel Crafts conditions to form an aryl alkanol. The aryl alkanol is then isolated and thereafter reacted with formaldehyde to cyclialkylate the alcohol.

In addition, several other references set forth processes for the production of isochromans such as U.S. Pat. No. 3,532,719 and U.S. Pat. No. 3,910,964 as well as U.S. Pat. No. 3,978,090.

The aforementioned references set forth production of compounds having the structures:

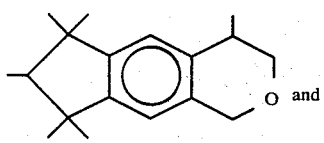
O and

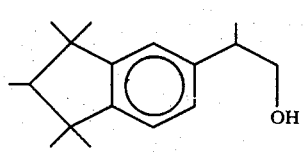
OH using as a precursor pentamethyl indane having the structure:

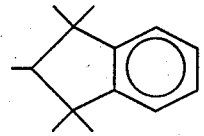

None of these references implies production of compounds having any of the structures:

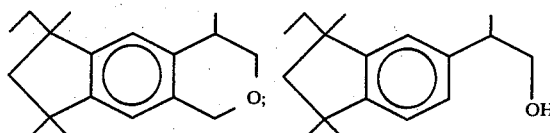

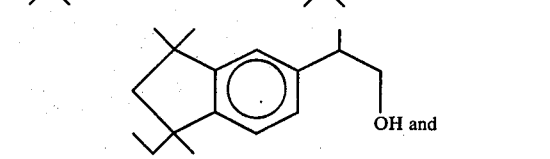

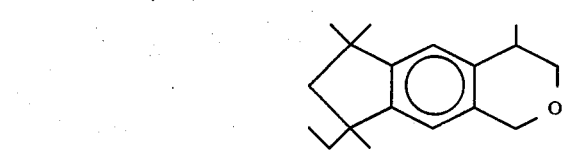

using as a precursor the tetraalkyl indane having the structure:

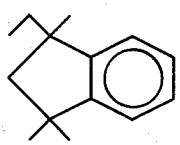

U.S. Pat. No. 3,400,159 issued on Sept. 3, 1968 entitled "Novel Musk-Like Substituted Acenaphthene and Process" discloses broadly at column 3, lines 42–61 that compounds having the formula:

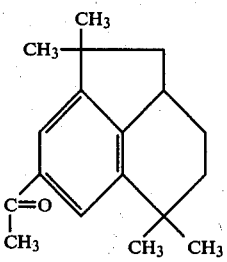

may be employed in "the same manner as other musk-like compounds alone or in admixture with other ingredients". It is further disclosed that such compounds may be used in perfumes, lotions, powders, soaps and the like containing one or more odorants or flavoring substances. The use of such compounds in foodstuffs, however, is not disclosed per se. Indeed, the statement that such compounds can be used "with other flavoring substances" is not preceded by an antecedent statement that there is utility of such compounds in flavoring or in augmenting, or enhancing the flavor of foodstuffs.

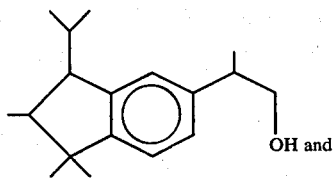

OH and

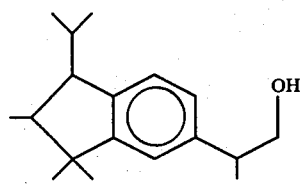

OH

Figure 2:
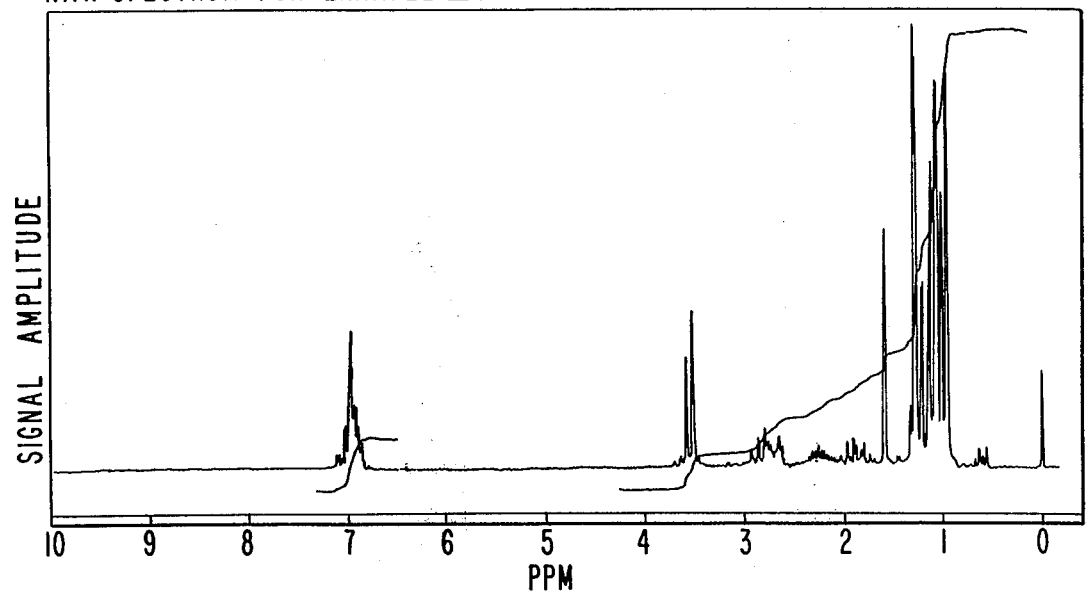

FIG. 2 is the NMR spectrum for compounds having the structures:

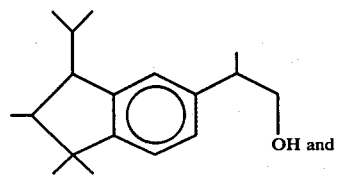

OH and

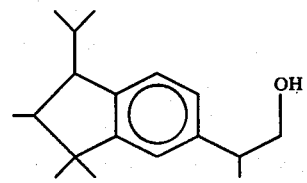

OH produced according to Example I.

Figure 3:
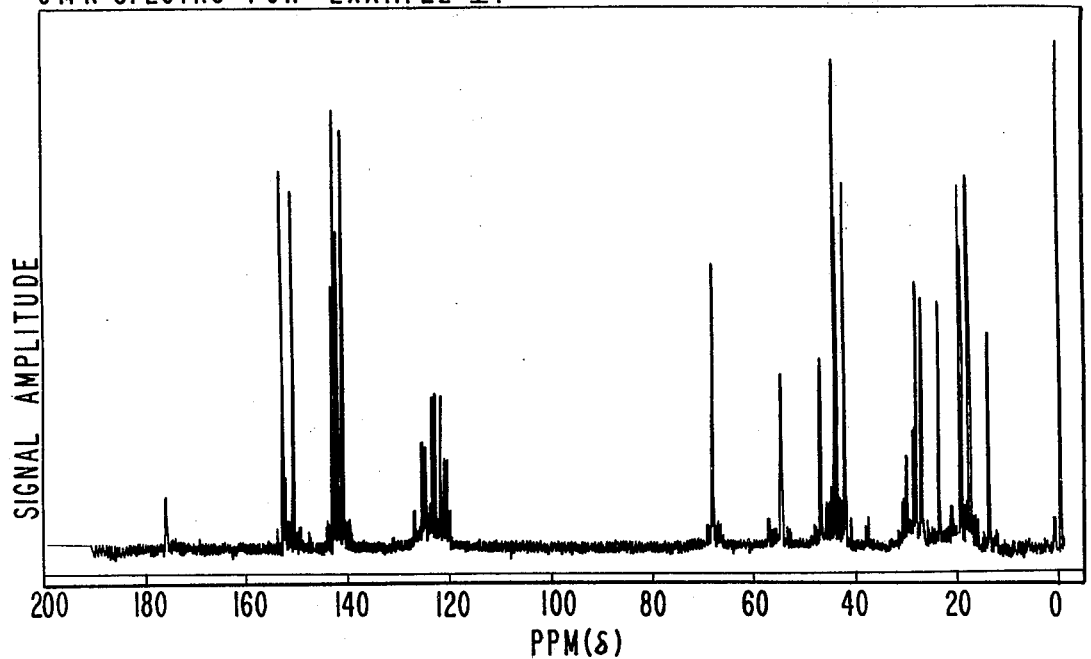

FIG. 3 is the CMR spectrum for compounds having the structures:

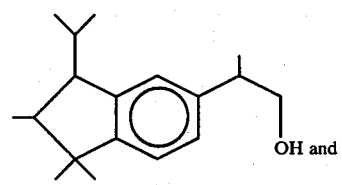

OH and

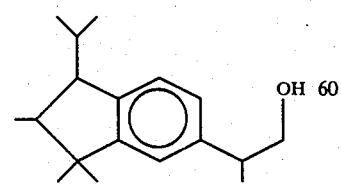

OH produced according to Example I.

Figure 4:
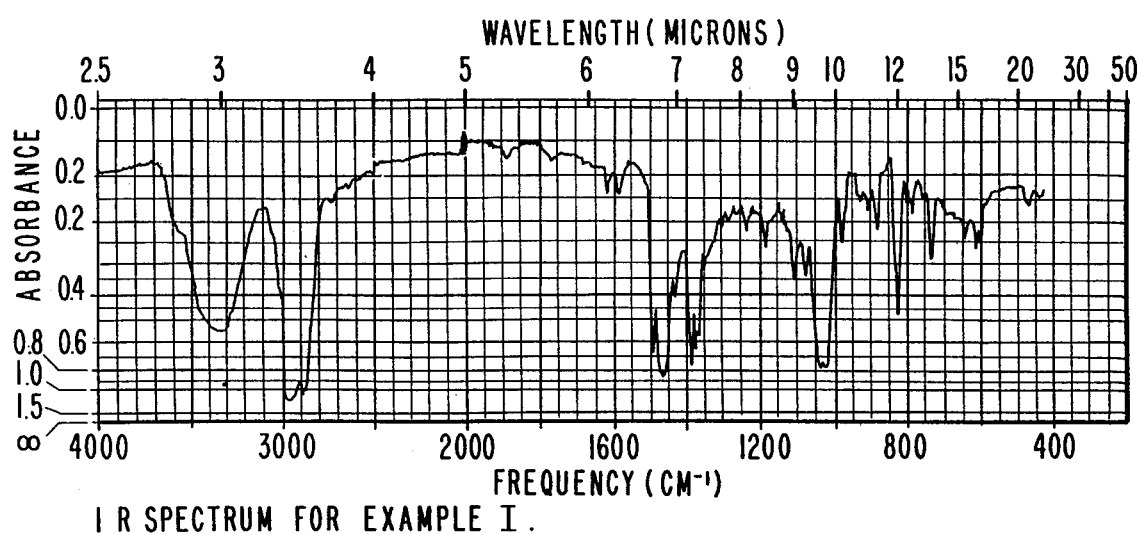

FIG. 4 is the infrared spectrum for compounds having the structures:

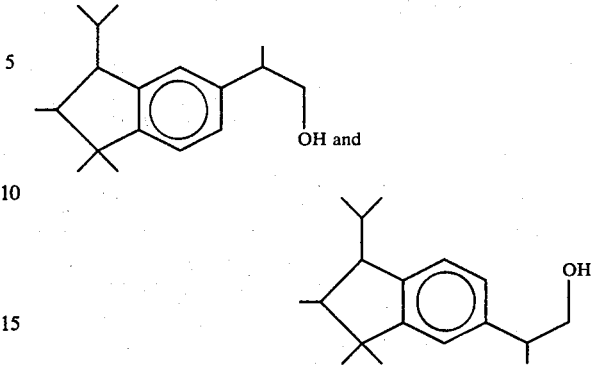

produced according to Example I.

Figure 5:
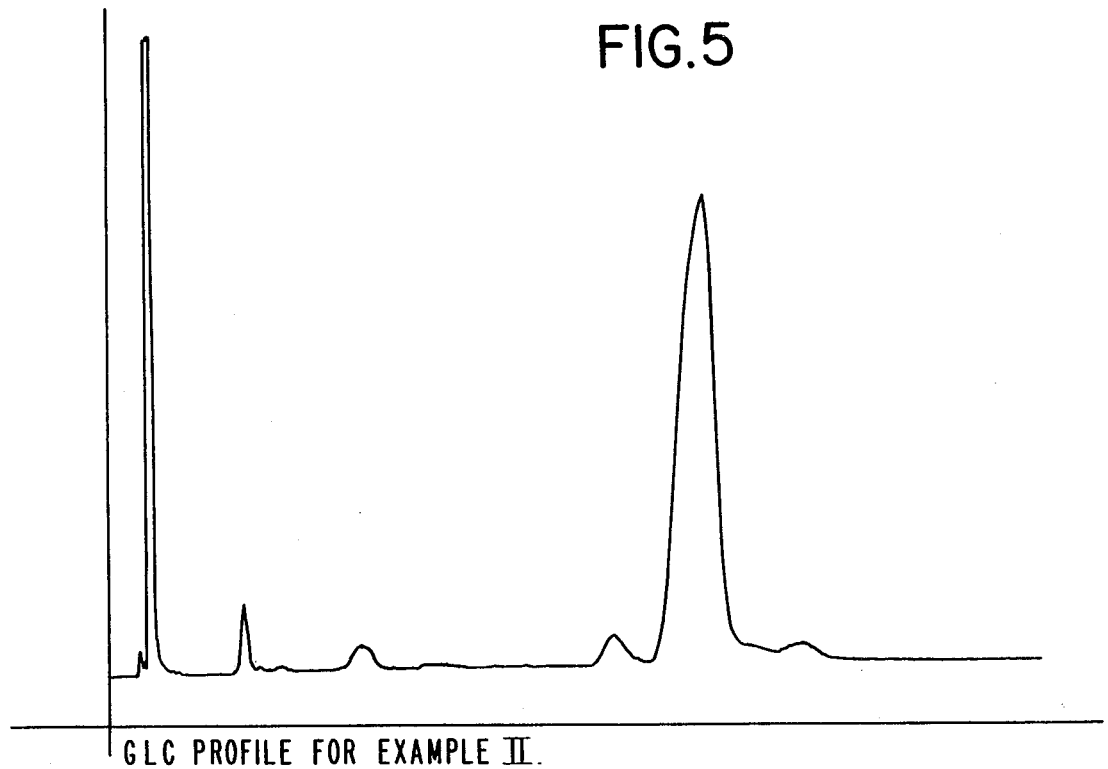

FIG. 5 is the GLC profile for compounds having the structures:

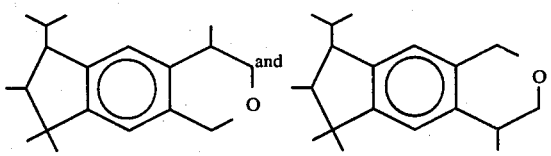

produced according to Example II.

Figure 6:
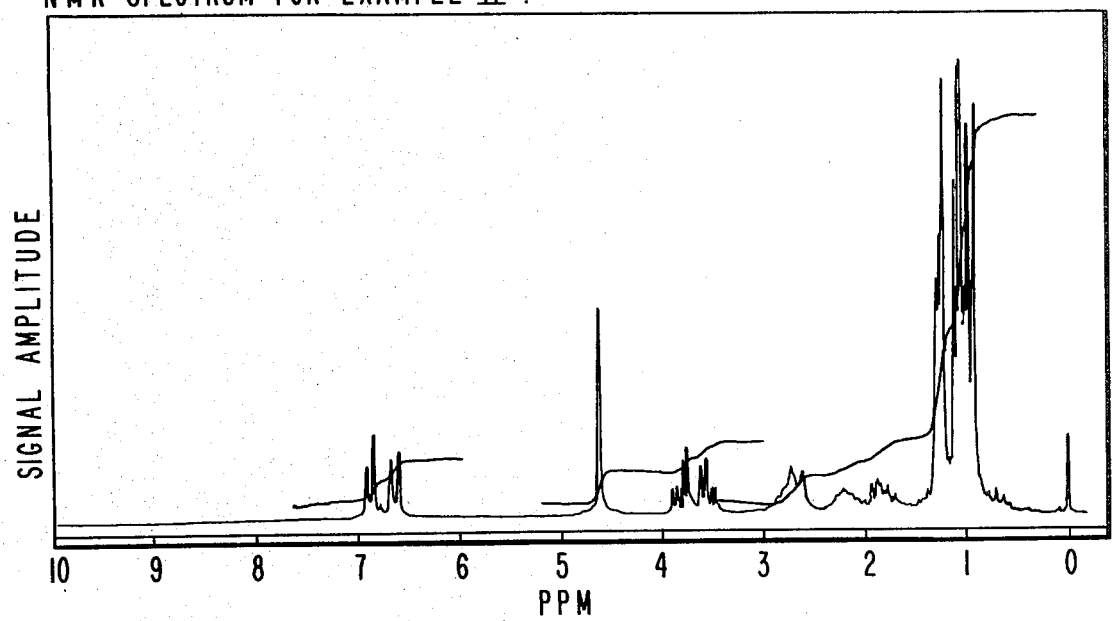

FIG. 6 is the NMR spectrum for compounds having the structures:

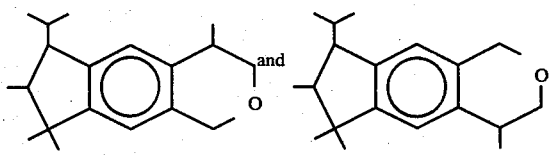

produced according to Example II.

Figure 7:
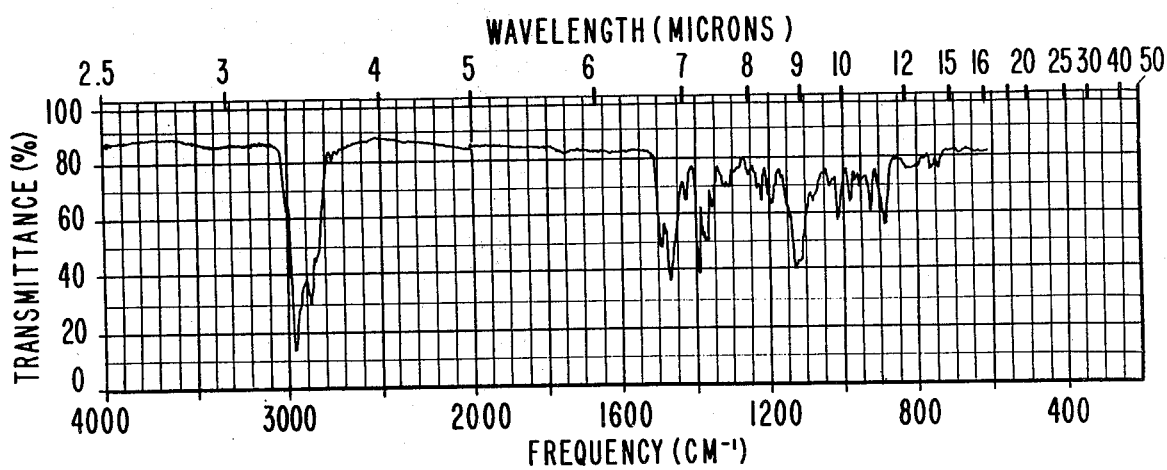

FIG. 7 is the infrared spectrum for compounds having the structures:

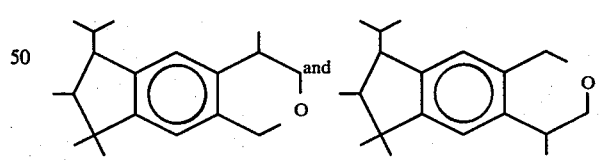

produced according to Example II.

Figure 8:
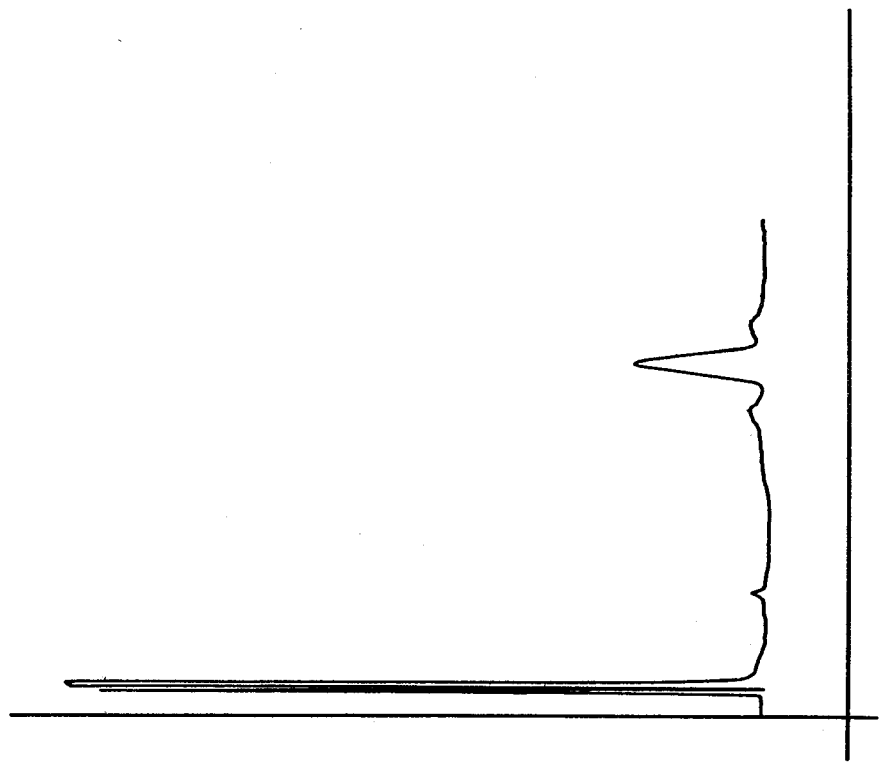

FIG. 8 is the GLC profile for compounds having the structures:

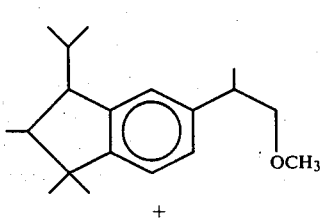

+

-continued

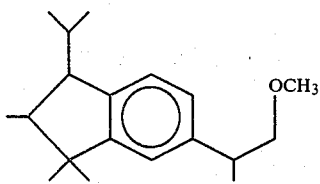

produced according to Example III.

Figure 9:
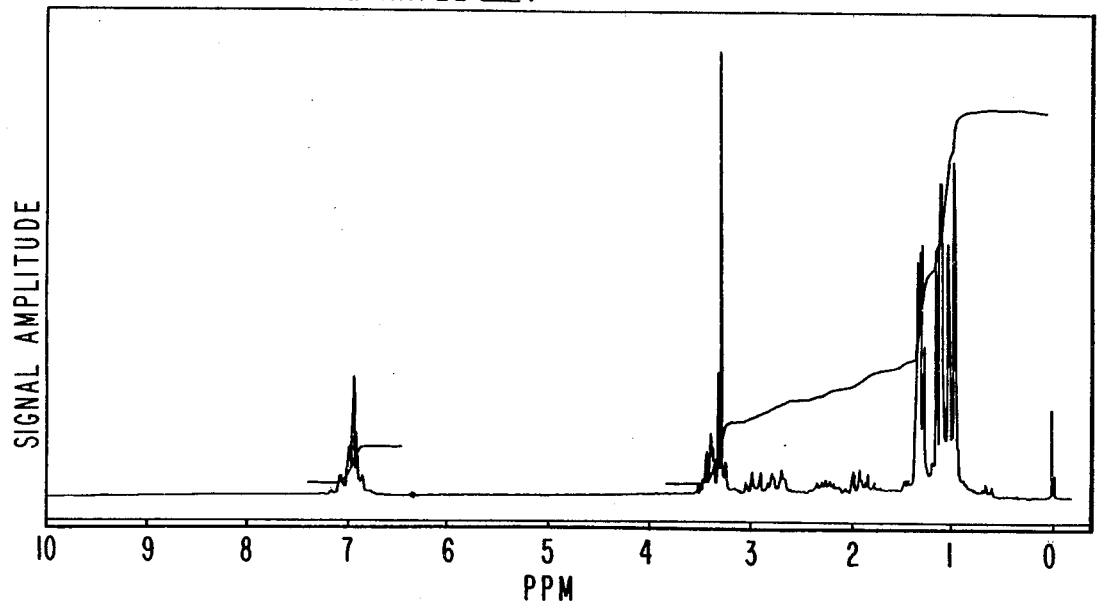

FIG. 9 is the NMR spectrum for compounds having the structures:

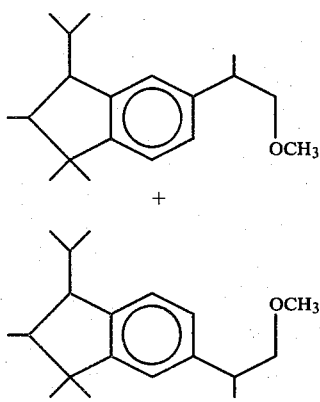

produced according to Example III.

Figure 10:
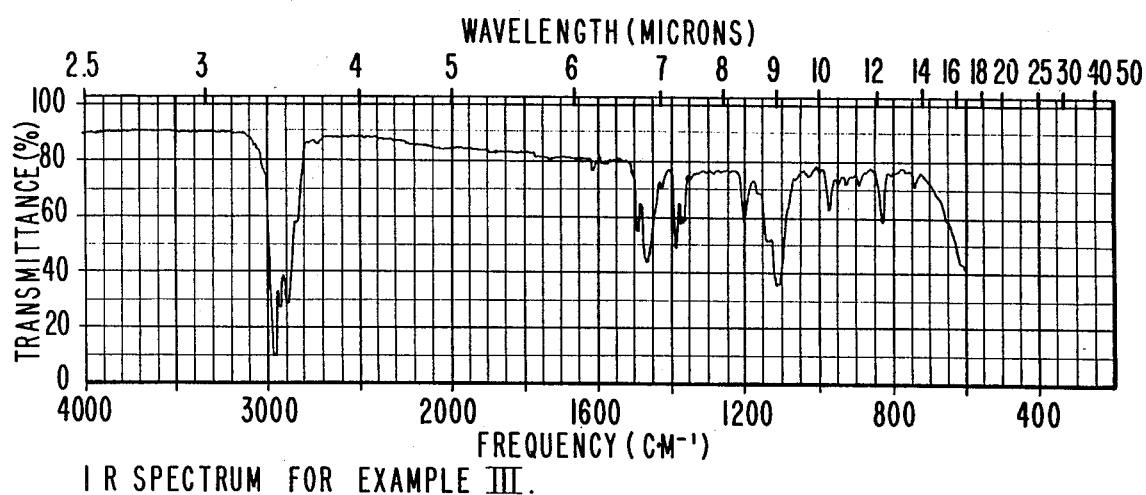

FIG. 10 is the infrared spectrum for compounds having the structures:

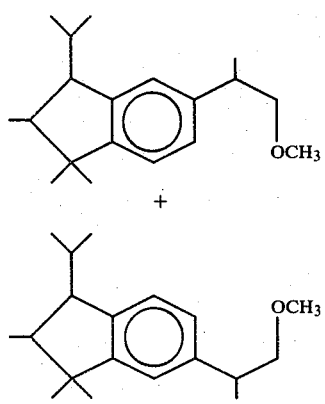

produced according to Example III.

FIG. 11 is the GLC profile for compounds having the structures:

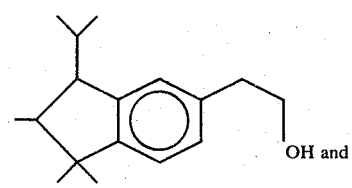

-continued

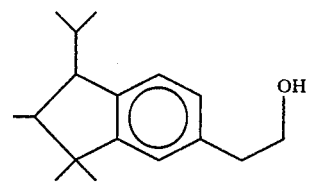

produced according to Example IV.

FIG. 12 is the NMR spectrum for compounds having the structures:

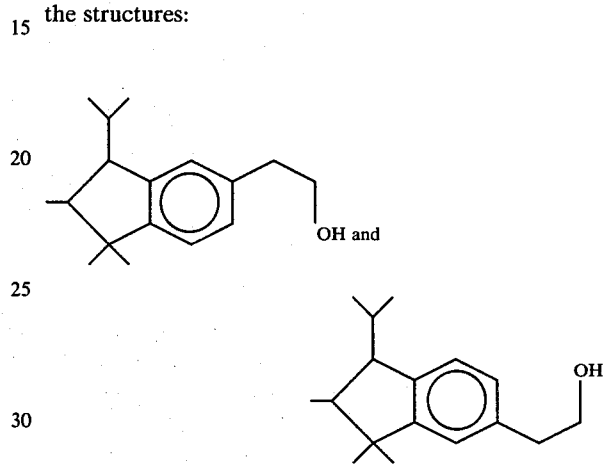

produced according to Example IV.

Figure 13:
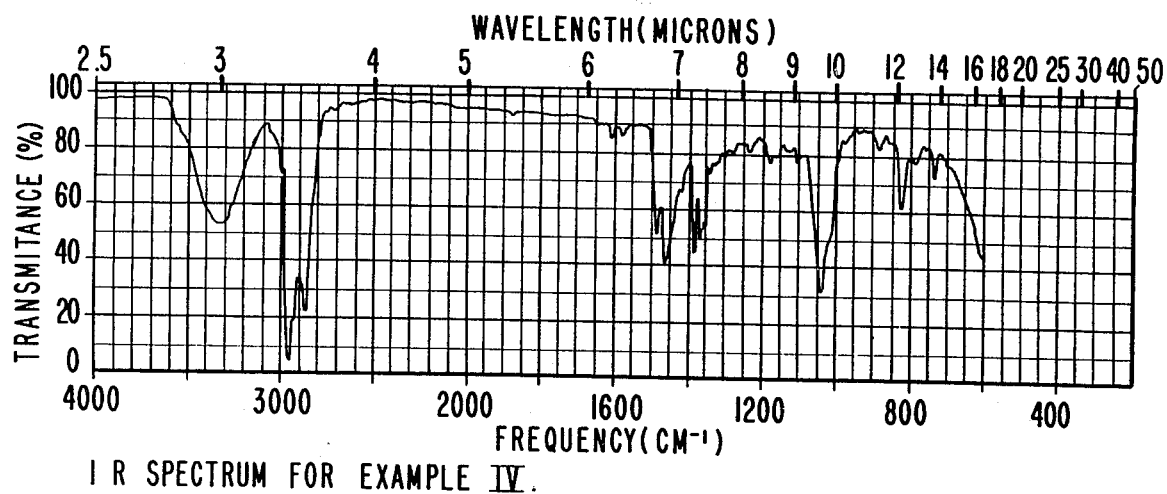

FIG. 13 is the infrared spectrum for compounds having the structures:

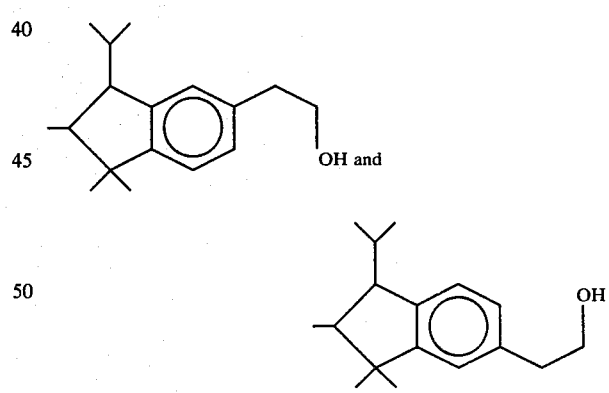

produced according to Example IV.

Figure 14:
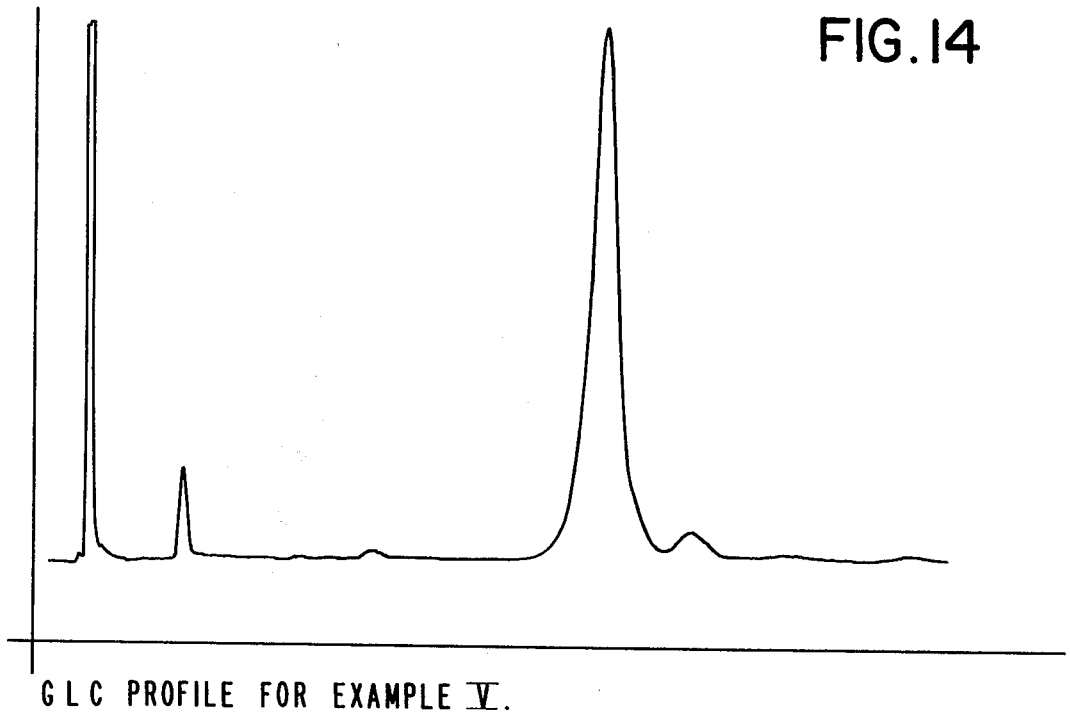

FIG. 14 is the GLC profile for compounds having the structures:

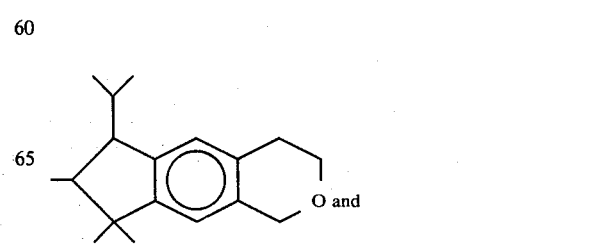

-continued

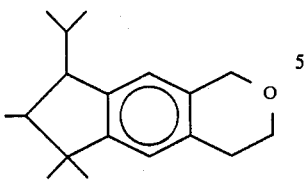

produced according to Example V.

Figure 15:
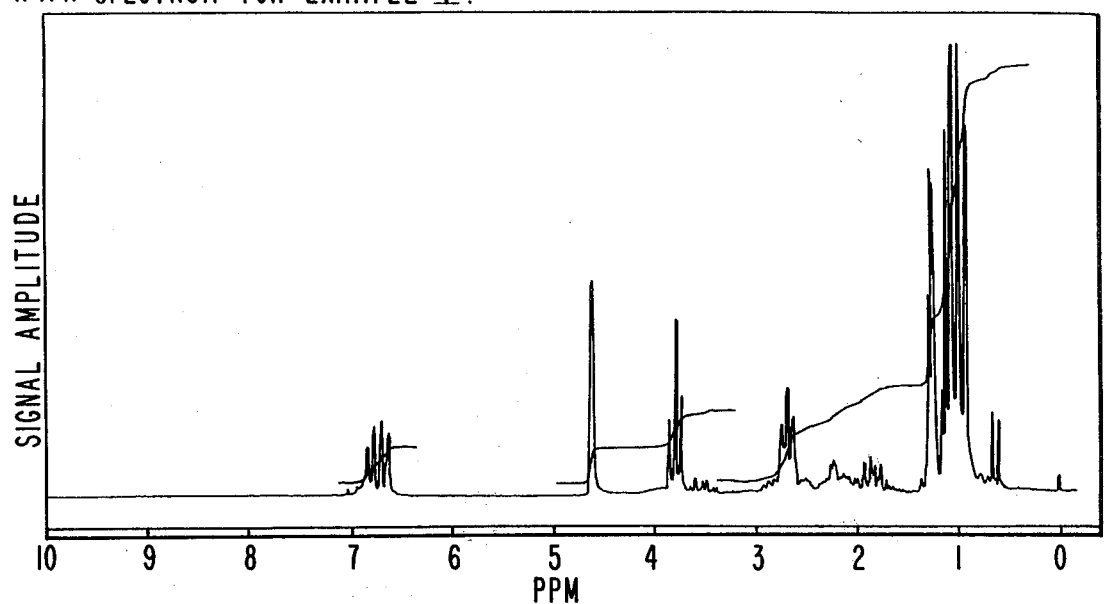

FIG. 15 is the NMR spectrum for compounds having the structures:

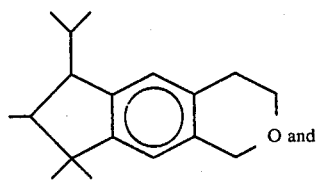

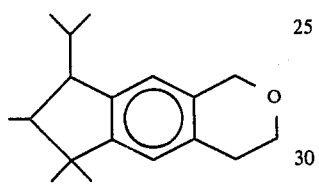

produced according to Example V.

Figure 16:
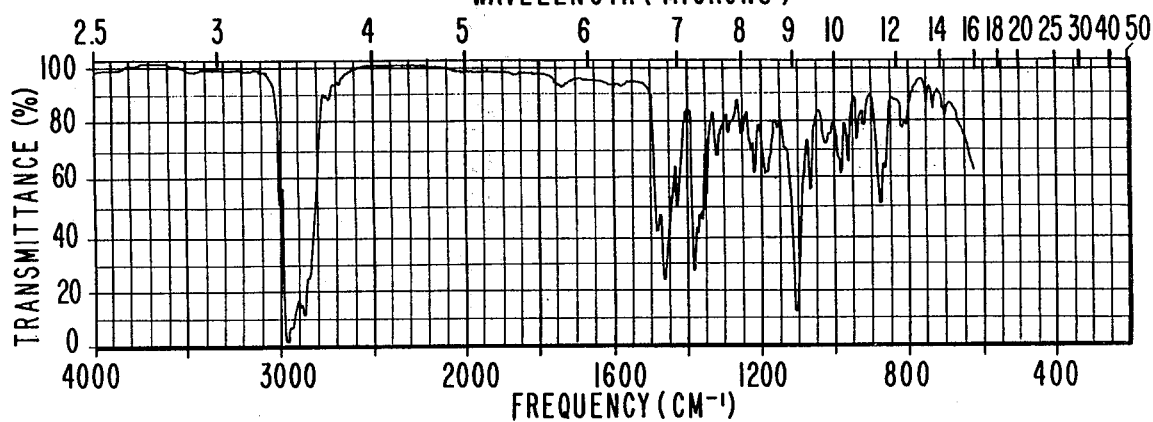

FIG. 16 is the infrared spectrum for compounds having the structures:

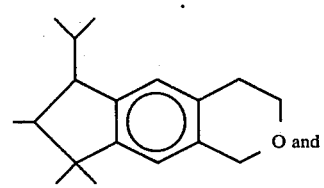

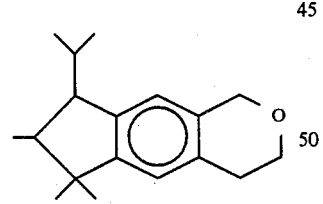

produced according to Example V.

THE INVENTION

It has now been discovered that novel solid and liquid foodstuff, chewing gum, medicinal products, and flavoring compositions therefor having pear, peach or apricot flavors with sweet, musky aroma characteristics and sweet and musky flavor characteristics and novel perfume compositions, colognes and perfumed articles having sweet, musky aromas may be provided by indane alkanols and tricyclic isochromans having the generic structure:

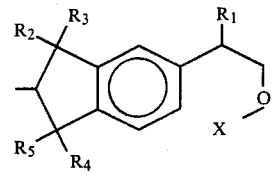

wherein $R_1$ is hydrogen or methyl; $R_2$, $R_3$, $R_4$ and $R_5$ represent hydrogen, ethyl or isopropyl; the dashed line represents a carbon-carbon single bond or no bond; X represents —$CH_2$—, $CH_3$ or hydrogen; with the proviso (i) that $R_2$ and $R_3$ represent methyl when $R_4$ is hydrogen and $R_5$ is isopropyl and $R_4$ and $R_5$ represent methyl when $R_2$ is hydrogen and $R_3$ is isopropyl; and the dashed line represents a carbon-carbon single bond when X is —$CH_2$—and the dashed line represents no bond when X is hydrogen or $CH_3$ and more specifically compounds having the structures:

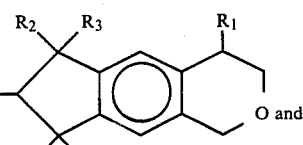

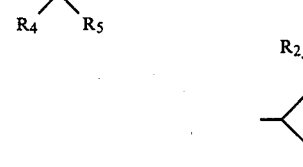

wherein $R_1$, $R_2$, $R_3$, $R_4$ and $R_5$ are defined as above.

The indane alkanols and tricyclic isochromans of our invention having the generic structure:

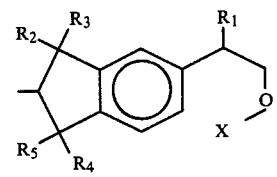

may be prepared according to processes illustrated by the following reaction schemes:

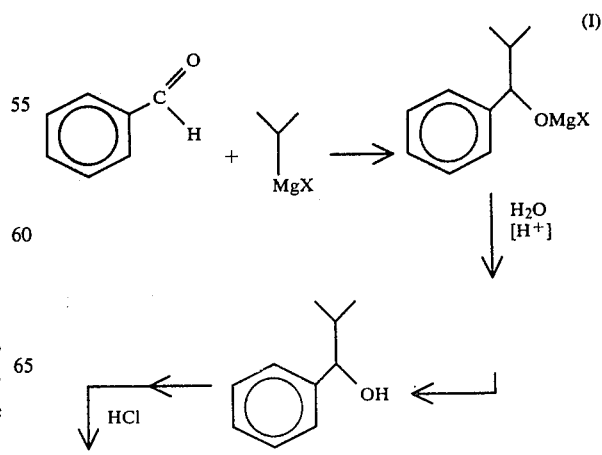

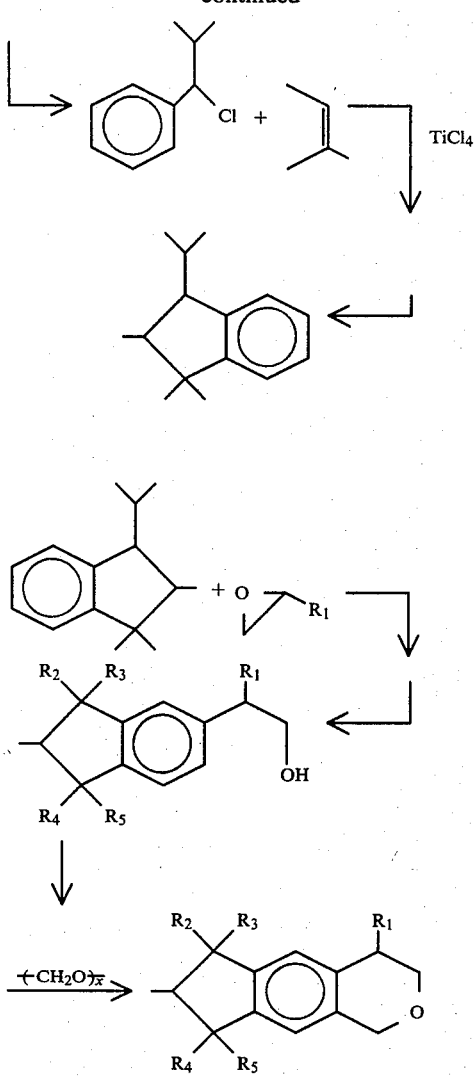

and the reacton of the tetraalkyl indane with the alkylene oxide, the reaction temperature may vary from 0° C. to 40° C. with the mole ratio of hydrocarbon starting material: epoxide being from 1:1 up to 5:1 with a ratio of 3:1 being optimum. The ratio of catalyst (Lewis Acid, such as aluminum trichloride):epoxide should be about 1:1. The reaction can be carried out in the present of a co-solvent, such as carbon tetrachloride, chloroform, dichloro benzene, acetone, hexane, or isooctane. In the second step, the cyclization of the indane alkanol to form the tricyclic isochroman, the reaction temperature should be in the range of 80° C. up to 150° C. with a mole ratio of starting indane alkanol: formaldehyde source being from 1:1 up to 3:1 with a ratio of 1.5:1 being optimum. The mole ratio of indane alkanol:formaldehyde source should be from 1:1 up to 3:1 with 2:1 being optimum. The mole ratio of paratoluene sulfonic acid to indane alkanol should be from 0.1 up to 0.4:1.

The process for producing the tricyclic isochroman may be in accordance with the processes set forth in Examples I and II of U.S. Pat. No. 3,910,964 issued on Oct. 7, 1975.

The indane alkanols and tricyclic isochromans of our invention are capable of supplying and/or potentiating certain flavor and aroma notes usually lacking in many food flavors, particularly peach flavors, apricot flavors and pear flavors. Furthermore, the indane alkanols and tricyclic isochromans of our invention are capable of supplying certain fragrance notes usually lacking in many perfume materials, for example, musk fragrances.

The indane alkanols and tricyclic isochromans of our invention have the following organoleptic properties:

TABLE I

FRAGANCE PROPERTIES

| COMPOUND MIXTURE | ORGANOLEPTIC PROPERTIES |
| --- | --- |
| Mixture of isochromans having the structures: 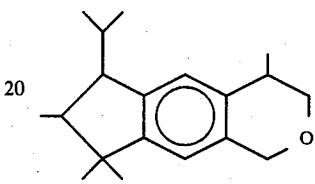 and 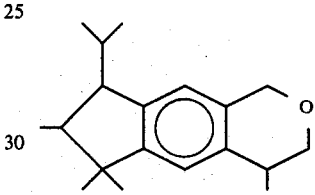 | A sweet, musky aroma. |
| Mixture of compounds having the structures: 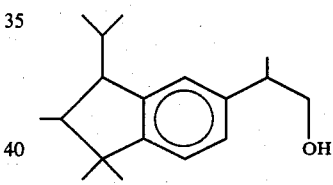 and 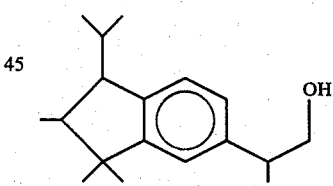 | A sweet, musky aroma with delicate animal musk nuances. |
| Mixture of compounds having the structures: 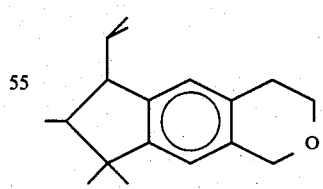 and 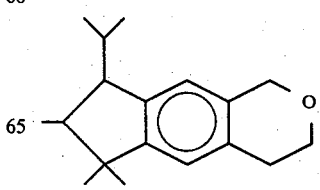 | A coarse, chemical musk note. |

TABLE II
FLAVOR PROPERTIES

| COMPOUND MIXTURE | ORGANOLEPTIC PROPERTIES |
|---|---|
| Mixture of compounds having the structures: 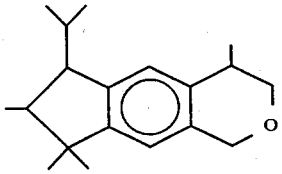 and 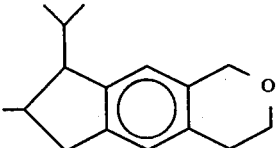 | A musky, animal aroma character with a sweet, musky flavor character at 1 ppm. |
| Mixture of compounds having the structures: 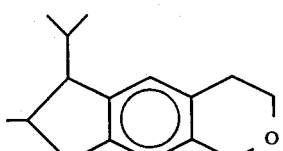 and 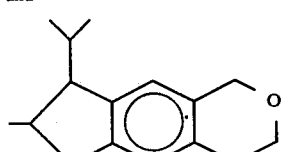 | A sweet, musky aroma and flavor characteristic at 0.002 ppm. |

When the indane alkanols and tricyclic isochromans of our invention are used as food flavor adjuvants, the nature of the co-ingredients included with said indane alkanols and tricyclic isochromans in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural synthetic flavors is deficient in some regard, or supplementing the existing flavor impression to modify its quality, character or taste".

As used herein, the term "enhance" is intended to means the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the indane alkanols and tricyclic isochromans of our invention, and, in addition, sweetening agents which may be sugars, including surcrose or dextrose and/or arrificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpast, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the indane alkanols and tricyclic isochromans encompassed within the scope of our invention. Also critical is the additional requirement that such material be nonreactive (within the range of storage conditions and room temperature use conditions) with indane alkanols and tricyclic isochromans.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim silk powder, hexoses, pentoses, disaccharides, e.g., sucrose, corn syrup and the like.

Surface active agents include emulsifying agents e.g., fatty acids such as capric acid, caprylic acid, palmitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like, firming agents such as aluminum sodium sulfate, calcium chloride and calcium gluconate; texturizers, anti-caking agents, e.g., aliminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chlroide, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methy-butyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans -3-buten-1-ol, ethanol, geraniol, 1-hexanol, 2-heptenol-1, trans-3-hexenol-1, cis-3-hexen-1-ol, 3methyl-3-buten-1-ol, 1-penten-2-ol, 1-penten-3-ol, p-hydroxyhenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl actate, methyl-n-butyrate, methyl caproate, methyl isobutyrate, alpha-methyl-n-butyrate, n-propyl acetate, n-amyl acetate, n-amyl-n- butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, delta-nonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanila; sulfides, e.g., methyl sulfide and other materials such as maltol, acetoin, acetals (e.g., 1,1-diethoxyethane, 1,1-dimethoxyethane and dimethoxymethane) and 2- and 3- cyclotetradecene-1-ones having one of the structures:

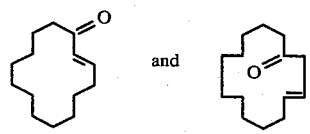

described in application for United States Letters Patent, Ser. No. 973,093 filed on Dec. 26, 1978.

The specific flavoring adjuvant selected for use may be either solid or liquid depending upon the desired physical form of the ultimate product, i.e., foodstuff whether simulated or natural, and should, in any event, be capable of providing an environment in which the indane alkanols and tricyclic isochromans can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of indane alkanols and tricyclic isochromans employed in a particular instance can vary over a relatively wide range whereby specific desired organoleptic effects (having particular reference to the nature of the product) are achieved. Thus, correspondingly greater amounts would necessary in those instances wherein the ultimate food composition to be flavored is relatively bland to the taste, whereas relatively minor quantitites may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se or flavoring composition.

The use of insufficient quantities of indane alkanols and tricyclic isochromans will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of indane alkanols and tricyclic isochromans ranging from a small but effective amount, e.g., 0.0001 parts per million up to about 50 parts per million by weight based on total composition are suitable. Concentrations in excess of the maximum quantity stated are not normally recommended, since they fail to provide commensurate enhancement or augmentation of organoleptic properties. In those instances wherein the indane alkanols and tricyclic isochromans are added to the foodstuff as an integral component of a flavoring composition, it is, of course, essential that the total quantity of flavoring compositon employed be sufficient to yield an effective concentration (of indane alkanols and tricyclic isochromans) in the foodstuff product.

Food flavoring compositions prepared in accordance with the present invention preferably contain the indane alkanols and tricyclic isochromans in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the indane alkanols and tricyclic isochromans with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mix are obtained by mixing the dried solid components, e.g., starch sugar and the like and indane alkanols and/or tricyclic isochromans in a dry blender until the requisite degree of uniformity is achieved.

It is presently preferred to combine with indane alkanols and tricyclic isochromans, the following adjuvants:
p-Hydroxybenyl acetone;
Geranoil;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;
Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma-decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine (4-allyl-1,2,6-trimethoxy benzene);
Isoelemecine (4-propenyl-1,2,6-trimethoxy benzene);
2-(4-hydroxy-4-methylpentyl) norbornadiene prepared according to U.S. Pat. No. 3,886,289; and
2- and 3-Cyclotetradecen-1-ones having the structures:

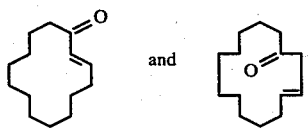

and described according to Application for United States Letters Patent, Ser. No. 973,093 filed on Dec. 26, 1978

The indane alkanols and tricyclic isochromans and one or more auxiliarly perfume ingredients including, for example, alcohols other than the indance alkanols of our invention, aldehydes, nitriles, esters, cyclic esters, ketones, ethers other than the tricyclic isochromans of our invention, natural essential oils and synthetic essential oils may be admixed so that the combined odors of the individual components produce a pleasant and desired fragrance, particularly and preferably, in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfurme compositions, it is the individual components which contribute to its particular olfactory characteristics, but the over-all effect of the perfume composition will be the sum of the effects of each of the ingredients. Thus, the indane alkanols and tricyclic isochromans can be used to alter the aroma characteristics of a perfume composition, for example, by utilizing or moderating the olfactory reaction contributed by at least one other ingredient in the composition.

The amount of indance alkanols and tricyclic isochromans of our invention which will be effective in perfume compositions depends on many factors including the other ingredients, their amounts and the effects which are desired. It has been found that perfume compositions containing as little as 0.01% of indane alkanols and tricylic isochromans and even less (e.g., 0.005%) can be used to impart a sweet, musk aroma for soaps, anionic, cationic, and nonionic detergents, fabric softener articles and compositions of matter, cosmetics or other products. The amount employed can range up to 10% of the fragrance components and can range up to 0.5% of the weight of the perfumed article and will depend upon considerations of cost, nature of the end product, the effect desired on the finished product and the particular fragrance sought.

The indane alkanols and tricyclic isochromans are useful, taken alone or in perfume compositions as olfactory components in anionic, cationic and nonionic detergents, soaps, fabric softener compositions, fabric softener articles for use in clothes dryer (e.g., "BOUNCE" ®, a registered trademark of the Procter & Gamble Company of Cincinnati, Ohio), space odorants and deodorants, perfumes, colognes, toilet water, bath preparations, such as lacquers, brilliantines, creams, deodorants, hand lotions and sun screens; powders, such as talcs, dusting powders, face powders and the like. When used as an olfactory component in perfume compositions or perfumed articles, such as anionic, cationic and nonionic detergents and in fabric softener compositions and fabric softener articles (e.g., for use in clothing dryers) as little as 0.05% of the indance alkanols and tricyclic isochromans of our invention will suffice to impart an intense sweet, musk fragrance. Generally, no more than 5% of the indane alkanols and tricyclic isochromans based on the ultimate end product is required in the perfume composition or in the perfumed article.

In addition, the perfume composition or fragrance composition of our invention can contain a vehicle or carrier for the indane alkanols and tricylcic isochromans. The vehicle can be a liquid such as a non-toxic alcohol, a non-toxic glycol, or the like. The carrier can also be an absorbent solid, such as a gum (e.g., gum arabic) or components for encapsulating the composition (such as gelatin) as by means of coacervation.

It will thus be apparent that the indane alkanols and tricyclic isochromans of our invention can be utilized to alter the sensory properties, particularly organoleptic properties, such as flavors and/or fragrances of a wide variety of consumable materials.

The following examples are illustrative and the invention is to be considered restricted thereto only as indicated in the appended claims. All parts and percentages given herein are by weight unless otherwise specified.

EXAMPLE I

Preparation of
3-Isopropyl-β,1,1,2-Tetramethyl-5-Indanethanol and
1-Isopropyl-β,2,3,3-Tetramethyl-5-Indanethanol Reaction:

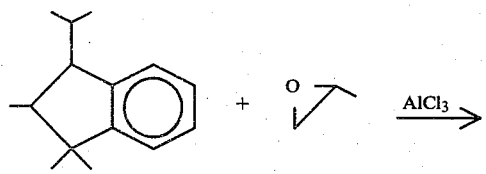

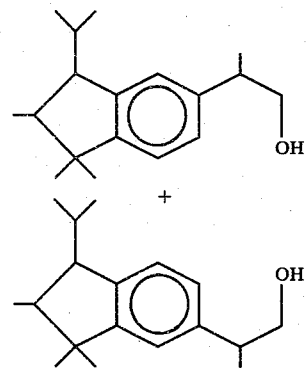

A well-stirred mixture of 1,1,2-trimethyl-3-isopropylindane (600 grams, isooctane (240 grams), and aluminum chloride (294 grams) is cooled to −10° C. To this stirred slurry is added a solution of 1,1,2-trimethyl-3-isopropylindane (410 grams), isocotane (240 grams), and propylene oxide via a subsurface addition inlet. The reaction mass is kept at −10° C. to −5° C. The addition is accomplished in three hours. After the addition, the mass is stirred at −10° C. for ten minutes and then poured into 4 liters of stirred ice water. After stirring 10 minutes, the bottom layer is discarded. The organic layer is washed with water, then aqueous sodium bicarbonate. Distillation through a short column affords 840 grams of recovered 1,1,2-trimethyl-3-isopropylindane and 225 grams of crude product. Fractional distillation through a 1″×12″ Goodloe ® packed column affords good-odored product consisting of a mixture of 3-isopropyl-β,1,1,2-tetramethyl-5-indanethanol and 1-isopropyl-β,2,3,3-tetramethyl-5-indanethanol(b.p. 142° C. at 1.2 mm Hg. pressure).

Figure 1:
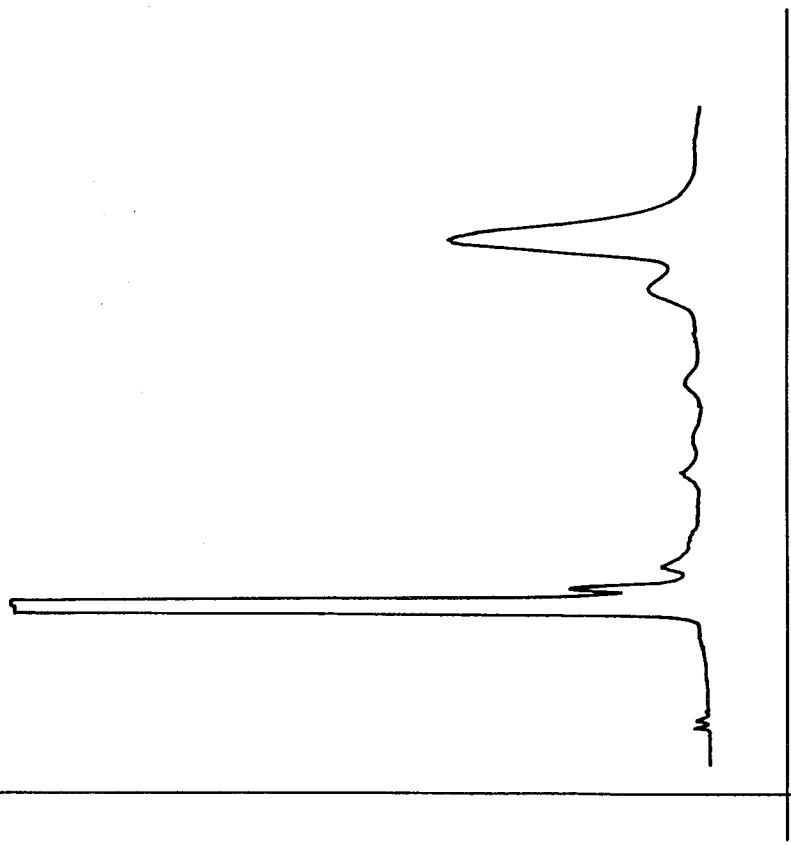
FIG. 1 represents the GLC profile for the reaction product of Example I containing compounds having the structures.

FIG. 1 shows a GLC trade of the crude product before fractional redistillation (¼″×10′, 10% SE-30 packed column, 220° C., isothermal).

FIG. 2 shows the NMR spectrum of Fraction 6 of the redistillation.

FIG. 3 shows the CMR spectrum of Fraction 6.

FIG. 4 shows the IR spectrum of Fraction 6.

EXAMPLE II

Preparation of
1,3,4,6,7,8-Hexahydro-6-isopropyl-4,7,8,8-Tetramethylcyclopenta[G]-2-Benzopyran and
1,3,4,6,7,8-hexahydro-8-Isopropyl-4,6,6,7-Tetramethylcyclopenta[G]-2-Benzopyran Reaction:

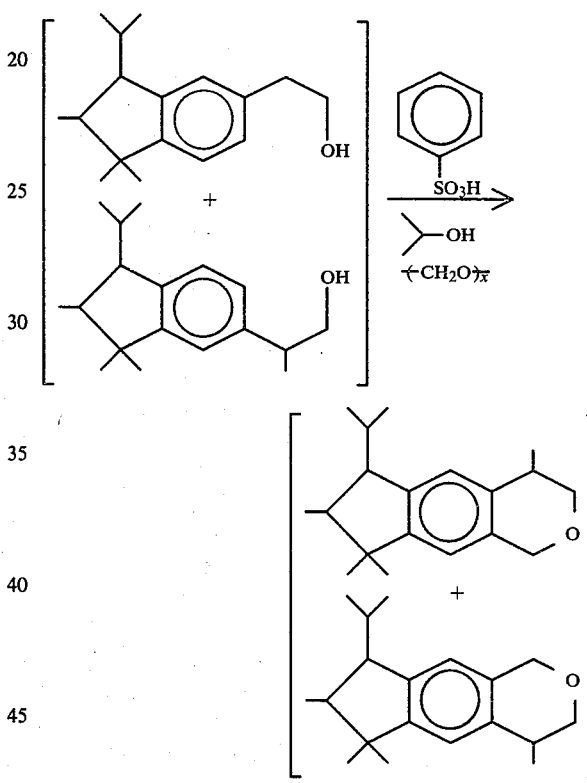

A stirred slurry of the indanethanol mixture (150 grams, as prepared in Example I), 20 grams of para-toluene-sulfonic acid, 65 grams of isopropyl alcohol and 21 grams of paraformaldehyde is heated to 93° C. (reflux) for three hours. The mass is then heated to 150° C. with concomitant distillation of lower boiling solvents. The reaction mass is aged three hours at 150° C., then cooled to 80° C. Toluene (100 mls) and 200 mls of 5% sodium hydroxide solution are added thereto with stirring. The mass is cooled and the aqueous (lower) layer is separated and discarded. The organic layer is washed with water and distilled through a short column to afford 153 grams of crude product. This material is fractionally redistilled through a 4 foot vigreux column to afford purified material. The mixture of 1,3,4,6,7,8-hexahydro-6-isopropyl-1,7,8,8-tetramethyl[G]-2-benzopyran and 1,3,4,6,7,8-hexahydro-6-isopropyl-1,7,8,8-tetramethylcyclopenta[G]-2-benzopyran (b.p. 135° C., 1.8 mm. Hg. pressure).

FIG. 5 is the GLC trace of the crude reaction product (¼"×10', 10% SE-30 packed column, 220° C., isothermal).

FIG. 6 is the NMR spectrum of Fraction 7 of the distillation.

FIG. 7 is the IR spectrum of Fraction 7 of the distillation.

EXAMPLE III

Preparation of
3-Isopropyl-β,1,1,2-Tetramethyl-5-Indanethyl Methyl Ether and
1-Isopropyl-β,2,3,3-Tetramethyl-5-Indanethyl Methyl Ether Reaction:

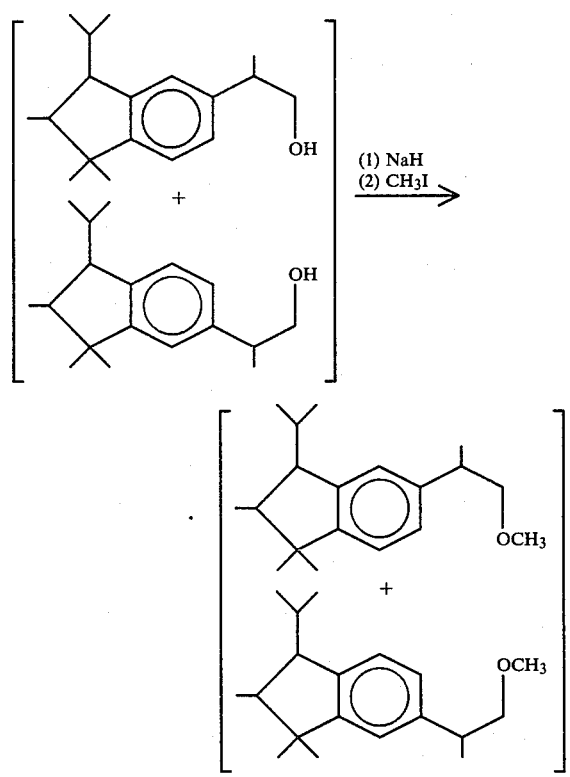

To a stirred slurry of 55% sodium hydride (18 grams) in 200 grams of toluene is added dropwise a solution of 50 grams of the alcohol mixture (as prepared in Example I) in 100 grams of toluene at 10° C. The slurry is stirred for 30 minutes until hydrogen gas evolution ceases. The temperature of the reaction mass is adjusted to 40° C. and a solution of 64 grams of methyl iodide in 50 grams of toluene is added dropwise in 30 minutes. The reaction mass is stirred for 15 minutes and then cooled. Three hundred mls of water are carefully added. The organic layer is separated and washed twice with water. Distillation through a short column affords 48 grams of crude product containing 3-isopropyl-β,1,1,2-tetramethyl-5-indanethyl methyl ether and 1-isopropyl-β,2,3,3-tetramethyl-5-indanethyl methyl ether. Redistillation through a 2' vigreux column with fractionation affords the product mixture in high purity (b.p. 125°–130° C. at 1.6 mm Hg. pressure).

FIG. 8 is the GLC trace of the crude reaction mass (¼"×10', 10% SE-30 packed column, 220° C., isothermal).

FIG. 9 shows the NMR spectrum of Fraction 5.

FIG. 10 shows the IR spectrum of Fraction 5.

EXAMPLE IV

Preparation of
3-Isopropyl-1,1,2-Trimethyl-5-Indanethanol and
1-Isopropyl-2,3,3-Trimethyl-5-Indanethanol Reaction:

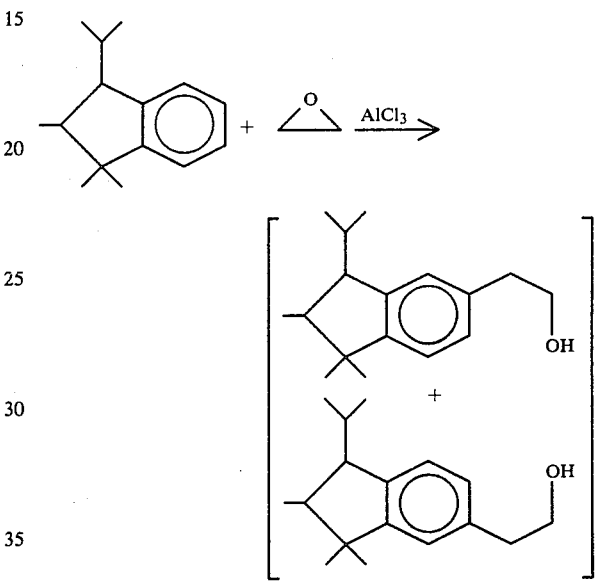

To a well-stirred mixture of 1,1,2-trimethyl-3-isopropylindane (1200 grams), isooctane (500 grams), and aluminum chloride (407 grams) is added over a three-hour period through a subsurface feed inlet, a solution of 840 grams of 1,1,2-trimethyl-3-isopropylindane, 340 grams of isooctane and 132 grams of ethylene oxide. External cooling is used to keep the temperature between −5° C. and 0° C. The reaction mass is stirred at −5° C. for 10 minutes, then poured quickly into 4 liters of well-stirred ice water. The reaction mass is stirred for 10 minutes then allowed to settle into two clear layers. The aqueous (bottom) layer is discarded and the organic layer is washed twice with water, neutralizing with sodium carbonate during the second wash.

The organic solution is distilled under vacuum to afford recovered isooctane and 1,1,2-trimethyl-3-isopropylindane. Also, 173 grams of a mixture of 3-isopropyl-1,1,2-trimethyl-5-indanethanol and 1-isopropyl-2,3,3-trimethyl-5-indanethanol are collected. This material is further purified by fractional distillation through a 1"×12" Goodloe ® packed column (b.p. 143° C. to 146° C. at 0.7 mm Hg. pressure).

FIG. 11 shows a GLC trace of the crude reaction mass before distillation (¼"×10', 10% SE-30 packed column, 220° C. isothermal).

FIG. 12 shows the NMR spectrum of Fraction 4.

FIG. 13 shows the IR spectrum of Fraction 4.

EXAMPLE V

Preparation of
1,3,4,6,7,8-Hexahydro-6-Isopropyl-7,8,8-Trimethylcyclopenta[G]-2-Benzopyran and
1,3,4,6,7,8-Hexahydro-8-Isopropyl-6,7,7-Trimethylcyclopenta[G]-2-Benzopyran Reaction:

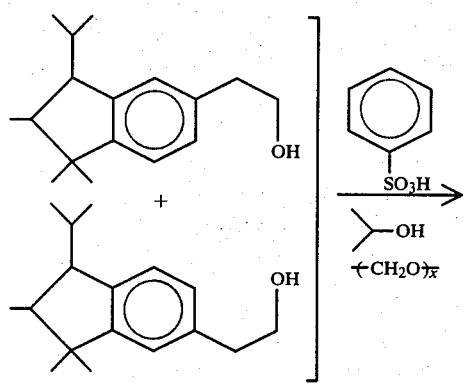

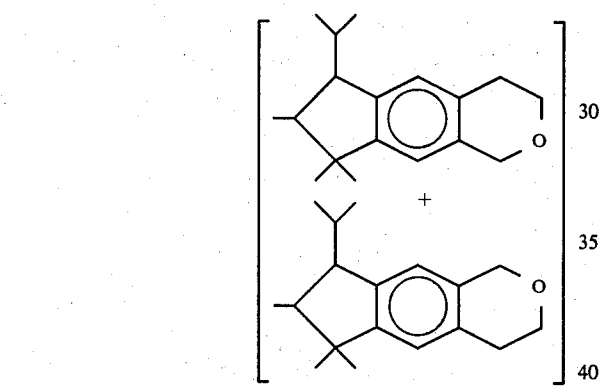

To a solution of 150 grams of the indanethanol (as prepared in Example IV) in 60 grams of isopropanol, is added 20 grams of para-toluene sulfonic acid and 25 grams of paraformaldehyde. The mixture is heated to reflux for 3 hours (90°-93° C.) with stirring. The temperature is then raised to 150° C. by distilling off lower boiling materials. The reaction mass is stirred at 150° C. for three hours, then cooled to 80° C. Toluene (100 mls) and 5% sodium hydroxide (200 mls) are added thereto with stirring. The mass is cooled and the aqueous (lower) layer is separated and discarded. The organic layer is washed with water and distilled through a short column to afford 137 grams of crude product. This material is fractionally distilled through a 2' vigreux column to afford a mixture of 1,3,4,6,7,8-hexahydro-6-isopropyl-7,8,8-trimethylcyclopenta[G]-2-benzopyran and 1,3,4,6,7,8-hexahydro-6-isopropyl-7,8,8-trimethyl-cyclopenta[G]-2-benzopyran.

FIG. 14 represents the GLC trace of the crude reaction mass.

FIG. 15 represents the NMR spectrum of Fraction 5 of the distillation.

FIG. 16 represents the IR spectrum of Fraction 5 of the distillation.

EXAMPLE VI

The following basic pear flavor formulation is prepared:

| Ingredients | Parts by Weight |
| --- | --- |
| Vanillin | 2.0 |
| Hexyl Acetate | 8.0 |
| Hexyl Isobutyrate | 20.0 |
| Trans-2-hexenal (10% in propylene glycol) | 2.0 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous, 95%) | 146.0 |
| Propylene glycol | 800.0 |

To a portion of the above basic pear flavor formulation, 0.02% by weight of the mixture produced according to Example II containing compounds having the structures:

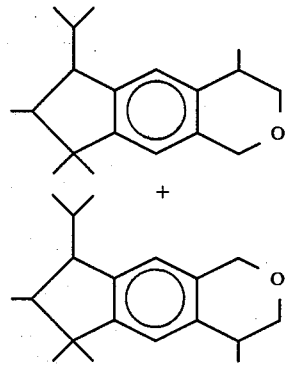

is added. To another portion of the basic pear formulation, nothing is added. Both flavor formulations are compared at the rate of 50 ppm in water and evaluated by a bench panel of four experienced tasters. All the tasters of the bench panel state that the flavor containing the mixture of compounds having the structures:

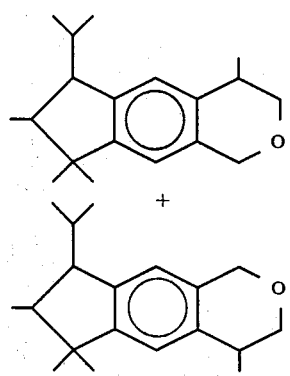

has a more natural riper pear character. This pear character is enhanced and longer lasting as a result of the addition of the mixture of compounds having the structures:

Therefore, the flavor formulation containing the compounds having the structures:

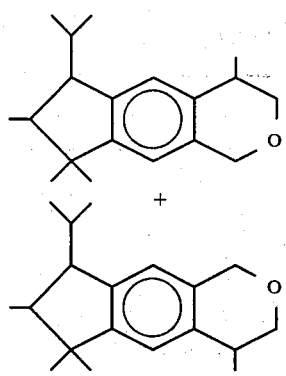

is preferred. When the individual compounds of the mixture are used in place of the mixture of compounds, the same result is attained.

EXAMPLE VII

Granular detergent compositions prepared according to United Kingdom Patent Specification No. 1,501,498 having the following formulae are prepared by spray-drying the following mixtures as indicated in the columns headed VII A, VII B, VII C and VII D.

|  | COMPOSITION IN % BY WEIGHT | | | | |
|---|---|---|---|---|---|
| Ingredient | Example VII A | Example VII B | Example VII C | Example VII D | Example VII E |
| Sodium salt of ethoxylated fatty alcohol sulfate having an average of about 2.25 moles of ethylene oxide per mole of fatty alcohol | 14.1 | 14.1 | 14.1 | 14.1 | |
| Sodium tallow alkyl sulfate | 2.4 | 2.4 | 2.4 | 2.4 | |
| Sodium silicate solids ratio: $SiO_2/Na_2O = 2.0$ | 0.0 | 2.0 | 6.0 | 6.0 | |
| Sodium silicate solids ratio: $SiO_2/Na_2O = 3.2$ | 1.0 | 0.0 | 0.0 | 6.0 | |
| Sodium tripolyphosphate | 24.0 | 24.0 | 24.0 | 24.0 | |
| $Na_{12}(AlO_2 . SiO_2)_{12}$ $27H_2O$ | 18.0 | 18.0 | 18.0 | 18.0 | |
| Moisture | 10.0 | 10.1 | 9.9 | 10.2 | |
| Sodium sulfate | 25.0 | 25.0 | 20.0 | 20.0 | |
| Minor ingredients including sodium toluene sulfonate, trisodium sulfosuccinate, dyes, and brighteners | 4.0 | 2.4 | 3.6 | 2.3 | |
| Mixtures of compounds produced according to Example I having the structures: | 1.5 | 0.0 | 0.0 | 0.0 | 0.0 |

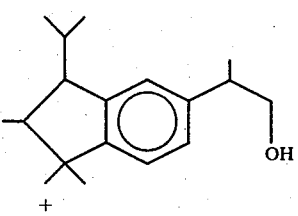

-continued

| Ingredient | COMPOSITION IN % BY WEIGHT | | | | |
|---|---|---|---|---|---|
| | Example VII A | Example VII B | Example VII C | Example VII D | Example VII E |
| Mixture of compounds having the structures: 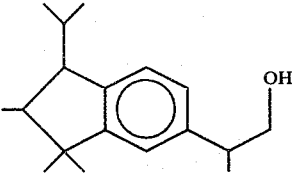 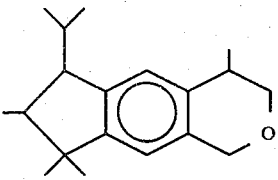 produced according to Example II. | 0.0 | 2.0 | 0.0 | 0.0 | 0.0 |
| Mixture of compounds having the structures: 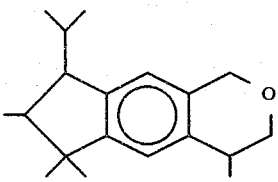 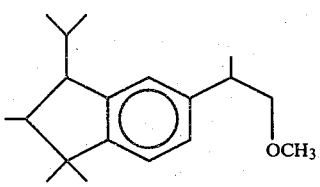 produced according to Example III. | 0.0 | 0.0 | 2.0 | 0.0 | 0.0 |
| Mixture of compounds having the structures: 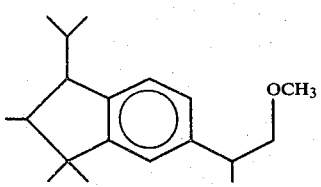 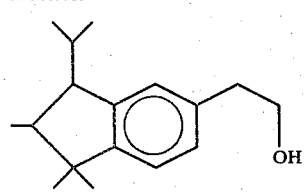 produced according to Example IV. | 0.0 | 0.0 | 0.0 | 3.0 | 0.0 |
| Mixture of compounds having the structures: 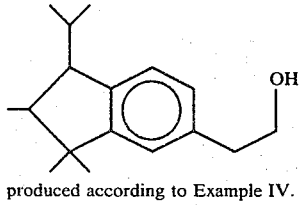 | 0.0 | 0.0 | 0.0 | 0.0 | 3.0 |

-continued

| | COMPOSITION IN % BY WEIGHT | | | | |
|---|---|---|---|---|---|
| Ingredient | Example VII A | Example VII B | Example VII C | Example VII D | Example VII E |
| 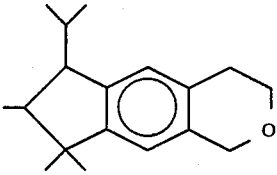  +  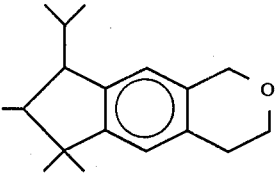  produced according to Example V. | | | | | |

Laundry solutions containing the above detergent compositions are used to launder fabrics. Each of the laundry compositions both prior to and on laundering gives rise to an intense sweet, musky aroma.

EXAMPLE VIII

Perfumed Liquid Detergent

Concentrated liquid detergents with a sweet, musky aroma are prepared containing 0.10%, 0.15% and 0.20% of the mixture of compounds produced according to Example V having the structures:

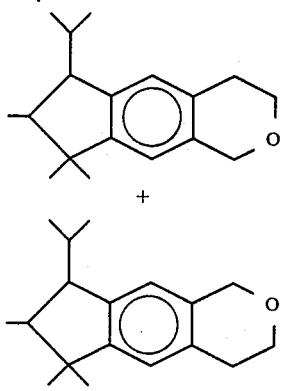

+

They are prepared by adding and homogeneously admixing the appropriate quantity of mixture of compounds having the structures:

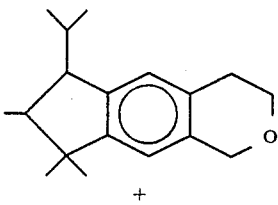

+

-continued

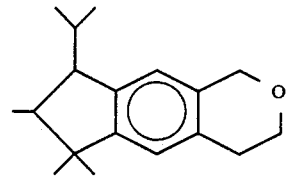

in the liquid detergent. The liquid detergent is a builder-free liquid detergent consisting of (a) 50% of a nonionic surfactant having an HLB of 8.0 and a critical micelle concentration of 0.007, weight % of 25° C.; (b) an ionic surfactant which is triethanolamine prepared according to United Kingdom Patent Specification No. 1,491,603.

The detergents all possess sweet, musky fragrances, the intensity increasing with greater concentrations of mixtures of compounds having the structures:

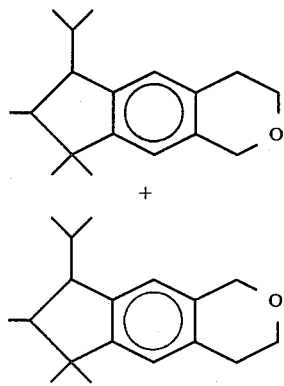

EXAMPLE IX

A. Powder Form

20 Grams of the flavor composition of Example VI which flavor composition contains a mixture of tricyclic isochromans having the structures:

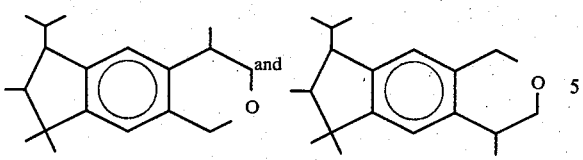

is emulsified in a solution containing 300 grams gum acacia and 700 grams water. The emulsion is spray-dried with a Bowen Lab Model Drier utilizing 250 c.f.m. of air with an inlet temperature of 500° F., and outlet temperature of 200° F. and a wheel speed of 50,000 r.p.m.

B. Paste Blend

The following mixture is then prepared:

| Ingredients | Parts by Weight |
|---|---|
| Liquid Flavor Composition of Example VI | 48.4 |
| Cab-o-Sil M-5 (Brand of Silica produced by the Cabot Corporation of 125 High Street, Boston, Mass., 02110); Physical Properties: Surface Area: 200m²/gm Nominal Particle Size: 0.012 microns Density: 2/3 lbs./cu.ft. | 3.2 |

The Cab-O-Sil is dispersed in the liquid flavor composition with vigorous stirring, thereby resulting in a viscous liquid. 48.4 Parts by weight of the powder flavor composition prepared in Part A is then blended into the said viscous liquid, with stirring at 25° C. for a period of 30 minutes, resulting in a thixotropic sustained release flavor paste.

EXAMPLE X

Chewing Gum

100 Parts by weight of chicle are mixed with 4 parts by weight of the flavor prepared in accordance with Example IX. 30 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing the chewing gum has a pleasant long-lasting pear flavor.

EXAMPLE XI

Toothpaste Formulation

The following separate groups of ingredients are prepared:

| Group "A" | |
|---|---|
| 30.200 | Glycerin |
| 15.325 | Distilled water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate |
| | (foaming agent) |
| Group "D" | |
| 1.200 | Flavor Material of Example IX |
| 100.00 (TOTAL) | |

PROCEDURE:

1. To ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE XII

Chewable Vitamin Tablets

The flavor material produced according to the process of Example IX is added to a Chewable Vitamin Tablet Formulation at a rate of 5 gm/kg which Chewable Vitamin Tablet Formulation is prepared as follows:

| Ingredients | Gms/Tablets |
|---|---|
| Vitamin C (Ascorbic acid) as ascorbic acid-solution mixture 1:1 | 70.0 |
| Vitamin B₁ (thiamine mononitrate) as Rocoat ® thiamine mononitrate 33% (Hoffman La Roche) | 4.0 |
| Vitamin B₂ (riboflavin) as Rocoat ® riboflavin 33⅓% | 5.0 |
| Vitamin B₆ (pyridoxine hydrochloride) as Rocoat ® pyridoxide hydrochloride 33⅓% | 4.0 |
| Niacinamide as Rocoat ® niacinamide 33⅓% | 33.0 |
| Calcium pantothenate | 11.5 |
| Vitamin B₁₂ (cyanocobalamin) as Merck 0.1% in gelatin | 3.5 |
| Vitamin E (dl-alpha tocopheryl acetate as dry Vitamin E acetate 33⅓% Roche | 6.6 |
| d-Biotin | 0.044 |
| Certified lake color | 5.0 |
| Flavor of Example IX | 5.0 |
| Sweetener-sodium saccharin | 1.0 |
| Magnesium stearate lubricant | 10.0 |
| Mannitol q.s. to make | 500.0 |

Preliminary tablets are prepared by slugging, with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lsting, consistently strong pear flavor for a period of 12 minutes.

EXAMPLE XIII

Musk Perfume Formulation

The following musk perfume formulation is prepared:

| Ingredients | Parts by Weight |
|---|---|
| Musk Ambrette | 200 |
| Musk Ketone | 200 |
| Beta Ionone | 50 |
| Vetiveryl Acetate | 50 |
| Sandlwood Oil | 100 |
| Benzoyl Benzoate | 400 |
| Mixture of tricyclic isochromans prepared according to Example II | 20 |

The mixture of tricyclic isochromans of Example II imparts to this musk formulation, a natural, sweet, musk aroma with great intensity.

EXAMPLE XIV

Preparation of a Soap Composition

100 Grams of soap chips are mixed with 1 gram of the perfume composition of Example XIII until a substantially homogeneous composition is obtained. The perfumed soap compositon manifests an excellent animal-musk, sweet, musk aroma.

EXAMPLE XV

Preparation of a Soap Composition

100 Grams of soap chips are mixed with 1 gram of the indane alkane mixture produced according to Example I until a substantially homogeneous composition is obtained. The perfumed soap composition manifests an excellent musk aroma.

EXAMPLE XV

Preparation of a Cologne and Handkerchief Perfume

The mixture of indane alkanol methyl ethers having the structures:

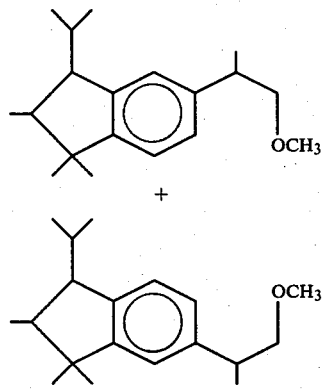

prepared according to Example III is incorporated into a cologne at concentrations of 1.5%, 2.0%, 2.5%, 3.0%, 3.5% and 4.0% in 85% aqueous ethanol; and into handkerchief perfumes at concentrations of 15%, 20%, 25% and 30% (in 95% aqueous ethanol). Distinct and definite sweet, musk fragrances are produced and imparted to the cologne and to the hankerchief perfume at each of the levels indicated.

EXAMPLE XVI

Preparation of a Cosmetic Powder Composition

A cosmetic powder is prepared by mixing in a ball mill, 100 grams of talcum powder with 0.15 grams of the mixture of indane alkanol methyl ethers produced according to Example III. The resulting powder has an excellent sweet, musk aroma.

EXAMPLE XVII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

| 1. | a water "dissolvable" paper ("Dissolvo Paper"); |
|---|---|
| 2. | Adogen 448 (m.p. about 140° F.) as the substrate coating; and |
| 3. | an outer coating having the following formulation (m.p. about 150° F.): 57 percent $C_{20-22}$ HAPS 22 percent isopropyl alcohol 20 percent antistatic agent 1 percent of the mixture of indane alkanols prepared according to Example IV having the structures: |

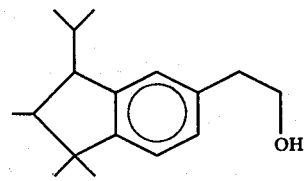

+

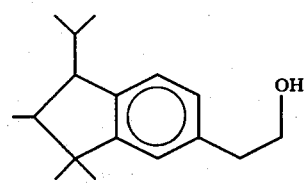

Fabric-softening compositions prepared as set forth above having an aroma characteristic which can be described as sweet and musky essentially consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. A sweet, musky aroma is imparted in a pleasant manner to the head space in the dryer on operation thereof using the said dryer added fabric softening nonwoven fabric. When the individual components of the mixture are used in place of the mixture, that is, the components having the structure:

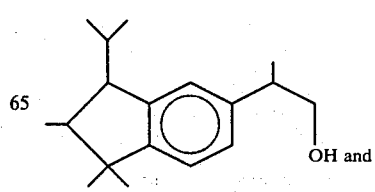

-continued

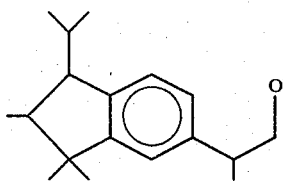

are used, a substantially identical result is achieved.

EXAMPLE XVIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and outer coating and the perfuming material are as follows:

| | |
|---|---|
| 1. | a water "dissolvable" paper ("Dissolvo Paper"); |
| 2. | Adogen 448 (m.p. about 140° F.) as the substrate coating; and |
| 3. | an outer coating having the following formulation (m.p. about 150° F.):<br>57 Percent $C_{20-22}$ HAPS<br>22 percent isopropyl alcohol<br>20 percent antistatic agent<br>1.5 percent of the compound having the structure:<br>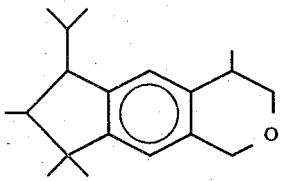<br>prepared according to Example II. |

A fabric-softening composition prepared as set forth above having an aroma characteristic which can be described as sweet and musky essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aroma is described as sweet and musky and is imparted in a pleasant manner to the head space in the dryer on operation thereof using the said dryer added fabric softening nonwoven fabric.

EXAMPLE XIX

Preparation of a Soap Composition

100 Grams of soap chips are prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide"

The resulting blend is then mixed with 1 gm of the compound having the structure:

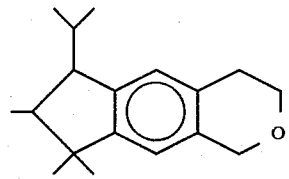

prepared according to Example V until a substantially homogeneous composition is obtained. The perfumed soap composition manifests an excellent sweet, musk aroma.

EXAMPLE XX

Preparation of a Soap Composition

100 Grams of soap chips are prepared according to Example V of U.S. Pat. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide"

The resulting blend is then mixed with 1 gm of the compound having thestructure:

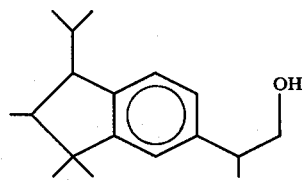

prepared according to Example I until a substantially homogeneous composition is obtained. The perfumed soap composition manifests an excellent sweet, musk aroma.

What is claimed is:

1. A mixture of compounds having the structures:

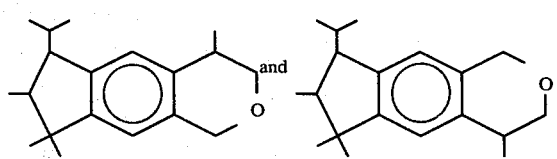

* * * * *